United States Patent
Stiller et al.

(10) Patent No.: US 7,485,114 B2
(45) Date of Patent: Feb. 3, 2009

(54) SYSTEM AND METHOD FOR THE CENTRAL CONTROL OF DEVICES USED DURING AN OPERATION

(75) Inventors: Heinz-Werner Stiller, Beringen (CH); Pavel Novak, Stetten (CH); Klaus M. Irion, Liptingen (DE)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 10/379,152

(22) Filed: Mar. 4, 2003

(65) Prior Publication Data
US 2003/0171740 A1 Sep. 11, 2003

Related U.S. Application Data

(63) Continuation of application No. PCT/EP01/10189, filed on Sep. 5, 2001.

(30) Foreign Application Priority Data
Sep. 5, 2000 (EP) ................................. 00119179

(51) Int. Cl.
*A61B 17/00* (2006.01)
(52) U.S. Cl. .................... 606/1; 600/101; 600/118; 600/539; 340/825
(58) Field of Classification Search ................ 600/101, 600/118; 340/825
See application file for complete search history.

(56) References Cited

U.S. PATENT DOCUMENTS

| | | | |
|---|---|---|---|
| 4,611,291 A * | 9/1986 | Hoelscher | 702/57 |
| 5,339,261 A * | 8/1994 | Adelson et al. | 714/47 |
| 5,553,237 A * | 9/1996 | Eisenberg et al. | 714/47 |
| 5,561,767 A * | 10/1996 | Eisenberg et al. | 714/47 |
| 5,572,999 A | 11/1996 | Funda et al. | 128/653.1 |
| 5,788,688 A | 8/1998 | Bauer et al. | 606/1 |
| 5,819,229 A | 10/1998 | Boppe | 705/2 |
| 6,120,435 A * | 9/2000 | Eino | 600/118 |
| 6,347,252 B1 * | 2/2002 | Behr et al. | 700/3 |
| 6,602,185 B1 * | 8/2003 | Uchikubo | 600/118 |
| 6,642,836 B1 * | 11/2003 | Wang et al. | 340/3.54 |

FOREIGN PATENT DOCUMENTS

| | | |
|---|---|---|
| EP | 0 747 279 A1 | 11/1996 |
| WO | WO 99/21165 | 4/1999 |

* cited by examiner

*Primary Examiner*—Linda C Dvorak
*Assistant Examiner*—Matthew J Kasztejna
(74) *Attorney, Agent, or Firm*—St. Onge Steward Johnston & Reens LLC

(57) ABSTRACT

The present invention relates to a system for the central control of devices (20, 52) used during an operation, comprising a first control unit (12) for control of said devices. The system is characterized in that a second control unit (14) is provided which is connected to the first control unit for exchange of information. The first control unit is embodied as closed system for control of at least those devices (20; 22-26) which carry out safety-related functions (safety-related devices), and the second control unit (14) is embodied as open system for control of the remaining devices (52) which carry out non safety-related functions (non safety-related devices). The invention further relates to a method for the central control of devices.

26 Claims, 1 Drawing Sheet

SYSTEM AND METHOD FOR THE CENTRAL CONTROL OF DEVICES USED DURING AN OPERATION

CROSSREFERENCES TO RELATED APPLICATIONS

This application is a continuation of copending international patent application PCT/EP01/10189 filed Sep. 5, 2001 and designating U.S., which claims priority of European Application EP 00 119 179.0 filed Sep. 5, 2000.

BACKGROUND OF THE INVENTION

The present invention relates to a system and a method for the central control of devices, particularly medical devices, which are used during an operation, comprising a first control unit for control of the devices.

For ergonomic reasons it is desirable to be able to remote control and control, respectively, the control device of all systems required during an operation from a central position, if possible out of a sterile area. Such a control may be carried out for example via a touch-screen (with a sterile cover) or via a voice control. The controlled devices and systems, respectively, may comprise for example endoscopic devices, as well as an op-table, op-lighting, room lighting, air conditioning, telephone, pager, internet, hospital-information system, consumption parts, management system and so on.

In view of the control of medical devices document DE 199 04 090 A1 for example discloses to interconnect single devices via a CAN-bus, the single devices being used as slaves and a host computer as master. All devices are controllable via this host computer.

The disadvantage of such a network is for example that the software- and hardware-efforts to be taken for the single host computer are very high since it has to be adapted to the device to be controlled having to fulfill the highest safety requirements. In view of devices to be controlled without having to fulfill these high safety requirements it may be possible that flexibility and simplicity of the handling may be lost.

If the single host computer is designed by applying a less stringent standard with respect to safety aspects, the risk would arise (for example for a PC with standard software like Windows-NT), however, said safety-related functions would be endangered by unreliable functions of non safety-related systems.

In this case it is assumed that the mentioned medical devices may be divided into two different groups, namely safety-related systems on the one hand, as for example endoscopic devices (insufflators, pumps, or RF-surgery and so on), op-table-control etc., namely devices or systems which may be life-threatening for a patient in the event of a breakdown or failure, and non-safety-related systems on the other hand, like picture archiving, material management systems, telephone remote control etc.

SUMMARY OF THE INVENTION

In view of the above the object of the present invention is to provide for a system and a method, respectively, which do not have the before mentioned disadvantages. Particularly it is to increase the safety in respect to the control of safety-related devices.

This object is solved by the system of the afore-mentioned kind by providing a second control unit which is connected with the first control unit for exchange of information, and the first control unit is embodied as a closed system for control of at least those devices which carry out safety-related functions (safety-related devices) and the second control unit is embodied as an open system for control of the remaining devices which carry out non safety-related functions (not safety-related devices).

This means in other words that the inventive system does not use a single host computer at has been done up to now, but uses two control units instead which are each assigned to different groups of devices to be controlled. When assigning the devices to be controlled to those control units it is assumed that there are generally devices for carrying out safety-related functions (for example endoscopic devices) and on the other hand devices for carrying out non-safety-related functions, like room lightening, air conditioning etc., during an operation.

In this connection the term "closed system" describes a system which does not allow any intervention from outside the system.

Such a system cannot be manipulated, reconfigured etc. neither by a user directly nor via the internet etc. In contrast thereto an open system may be configured or for example supplemented by a user. Here, interventions and manipulations, respectively, from outside are possible.

The advantage of the inventive system is among others that the provision of a further control unit increases the safety with respect to undesired erroneous or faulty functions without limiting the flexibility of the whole system thereby. Due to the fact that on the second control unit software may be used which have not to fulfill such stringent safety requirements as it is the case for the control of safety-related devices, standard software may be used so that the single investment costs on the one hand as well as the running maintenance costs of the total system on the other hand may be reduced.

A further advantage of the inventive system is that the first control unit which is responsible for the control of the safety-related devices is embodied as a closed system which secures that all attempts to manipulate the operating system are disabled. Moreover also manipulations of the applications for controlling the safety-related devices are impossible.

At this point it is to be noted, however, that on the first control unit also applications for control of non safety-related devices could run provided that these applications have been tested under safety aspects before.

Advantageously, those control units are each part of independent computers (PC's). Of course, it is also contemplated that those control units are integrated in one computer which comprises at least two processors (CPU) with one control unit being realized by one processor.

When using a single host computer and considering such requirements it would not be possible to carry out the control of non safety-related devices with the desired simplicity and flexibility. Moreover the risk would always arise that erroneously programmed software for the non safety-related devices would influence the control of safety-related devices.

In a preferred embodiment the first control unit and the safety-related devices are interconnected via a bus-system preferably the Karl Storz-communication-bus (SCB®). Preferably, the non safety-related devices and the second control unit are interconnected via a further bus-system, both bus-systems preferably being different.

These measures result in a simplification of the system as well as to a reduction of the total costs since the especially designed bus-system for safety-related functions is not used for the control of every devices. Rather also conventional standard bus-systems may be used. Hence the expensive safety bus-system is only used for the interconnection of the safety-related devices.

In a preferred embodiment an interface unit is provided which is connected with both control units on the one hand and with peripheral devices on the other hand and which connects each of the control units with the peripheral devices. Preferably, the interface unit is controlled by the first control unit via a control line. More preferably the peripheral devices comprises a monitor device and/or an input device, preferably a keyboard and a mouse. More preferably, the monitor device is provided as a touch-screen also allowing an input.

These above mentioned measures result in the advantage that the costs for the total system are reduced on the one hand and the handling is significantly simplified on the other hand since the peripheral devices required for input of control instructions or for monitoring of parameters are provided only once. The surgeon has not to observe plural monitor devices hence. Further, the control line between the interface unit and the first control unit guarantees that the control unit controlling the important safety-related devices also allows the respective necessary function and displays the important safety-related parameters on the touch-screen in case of a breakdown and an failure, respectively, of the second control unit. Altogether, also an increase of the safety level of the system is achieved.

In a preferred embodiment the second control unit comprises a receiving means to capture error messages from the first control unit and to display them on one of the peripheral devices.

This measure has the advantage that also in case of a connection of the second control unit with the interface unit for the control of non safety-related devices error messages concerning safety-related devices are immediately provided to the user of the system. It may hence be avoided that the display of such error messages is only signaled to the user upon re-switching the connection from the first control unit to the peripheral devices. Consequently, this has the advantage that the safety of the total system is further increased.

Preferably the safety-related devices include endoscopic devices, preferably insufflators, pumps, light sources, video devices and for example op-table-controllers etc. The non safety-related devices include for example picture archiving, op-lighting, room lighting, telephone, air conditioning, pager, internet, hospital system, consumption parts, management systems, etc.

It is further preferred to interconnect both control units via an Ethernet-bus (TCP/IP-protocol), since this type of bus-system has been proved as reliable and cost effective.

In a preferred embodiment the first control unit comprises an embedded operating system, preferably "embedded windows NT", which is protected against interventions from outside the system.

This means in other words that the operating system of the first control unit is a fixed component of the unit and is hence protected against manipulations. The user may not carry out any interventions into the operating system. This would be possible for example with current PC's. Hence, it is avoided that specific safety-related functions can not be carried out anymore or are carried out erroneously due to intentional or unintentional interventions into the operating system.

In a preferred embodiment the first control unit comprises a check means which cyclically checks the connection with the interface unit and outputs an error message if a connection is not present.

Also this measure results in an increase of safety because the system signalizes the user immediately when a display and a setup, respectively, of respective parameters of safety-related devices are not possible anymore due to the failure of the interface unit.

In a preferred embodiment the first control unit comprises a voice control, for example in form of a software module.

This measure has the advantage that the operation by the surgeon is simplified.

The object underlying the present invention is also solved by a method for the central control of devices used during an operation in that the devices for the control of safety-related functions are controlled by a first control unit and the devices for carrying out non safety-related functions are controlled by a second control unit.

This method allows to realize the advantages mentioned in connection with the afore-mentioned inventive system in the same manner so that the advantages may not be described here anymore.

In a preferred embodiment both control units communicate with each other, while preferably the first control unit checks the second control unit for faults. It is further preferred to provide for an interface unit which is controlled by the first control unit and which in response thereto forwards signals either from the first or the second control unit to a common peripheral device.

This measure has—as already mentioned—the advantage that the costs of the system are reduced and the ease of operation is increased.

In a preferred embodiment the first control unit will drive the interface unit in case of a failure of the second control unit such that the signals of the first control unit are forwarded to the peripheral devices.

This means in other words that the first control unit ensures that a failure in the second control unit does not result in the breakdown of the connection between the first control unit and the peripheral devices.

In a preferred embodiment the interface unit forwards the signals of the first control unit to the peripheral devices immediately if a safety-related function is to be carried out.

This measure has the advantage that the important functions are possible also when the present connection between the second control unit and the peripheral devices is present. The result is an increase of safety.

In a preferred embodiment the interface unit forwards the signals of the second control unit to the peripheral devices after activating a non safety-related function only when the safety-related function is completed and completely carried out, respectively. This means in other words that the execution of safety-related functions cannot be interrupted by switching the interface unit. Rather, the execution of the safety-related function is carried out up to the end and only than the interface unit will build up the connection between the second control unit and the peripheral devices.

Further advantages and embodiments of the invention can be taken from the following description and the enclosed drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWING

The invention will now be described in detail with reference to a FIGURE, the FIGURE showing a schematic block diagram of an inventive system.

DETAILED DESCRIPTION OF PREFERRED EMBODIMENTS

Figure 1:
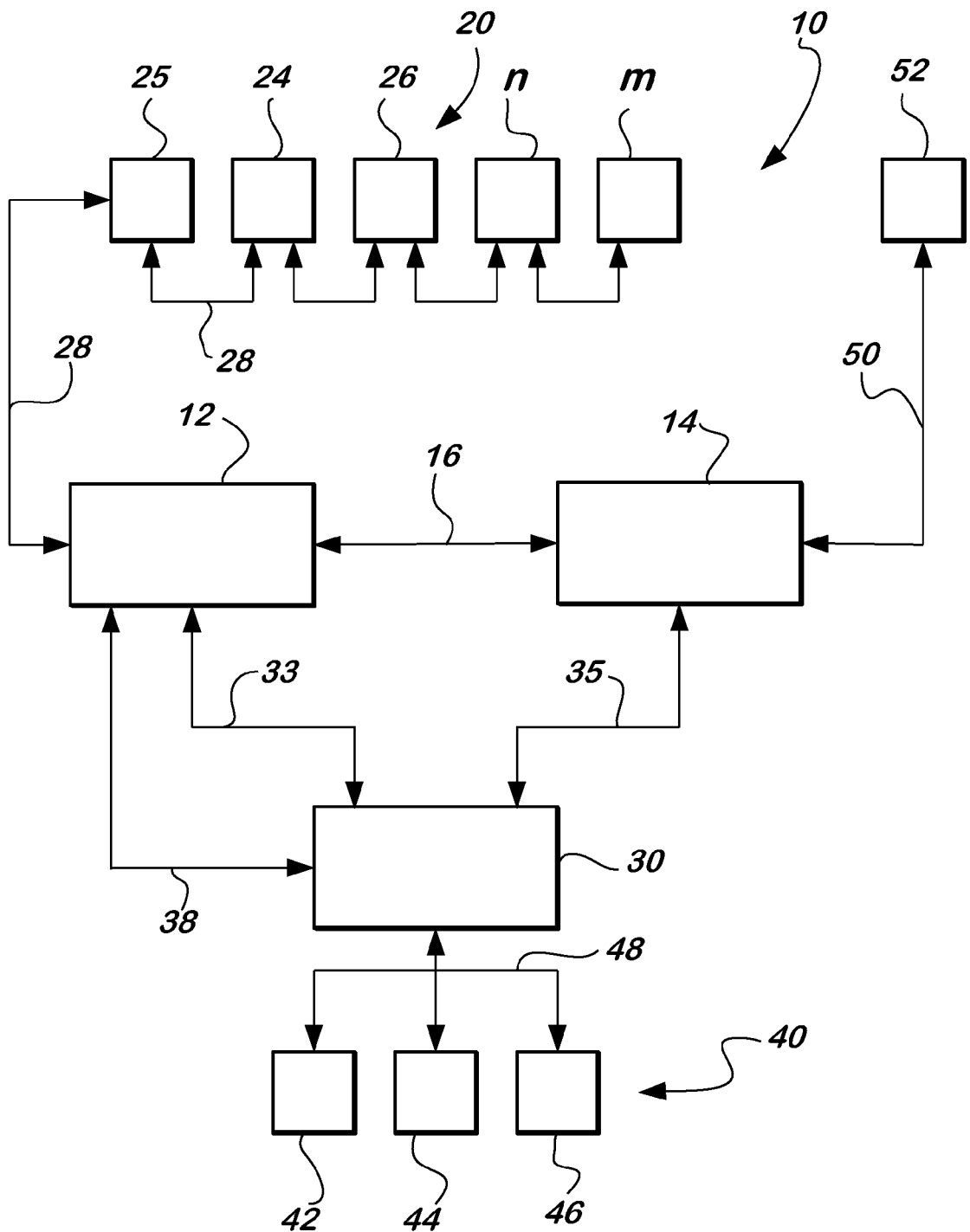

In the FIGURE a system for the central control of devices used during an operation is shown as a block diagram and is indicated with reference numeral 10. The system 10 comprises a first computer unit 12 and a second computer unit 14. Both computer units 12, 14 are interconnected via a bus-connection 16, for example an Ethernet-bus-connection, in order to exchange data in form of messages.

Both computer units 12, 14 are provided as medical PC's, wherein the first computer unit 12 uses an embedded operating system, preferably an "embedded windows NT"-operating system. The second computer unit 14 operates preferably with a common windows operating system or an other non embedded operating system.

The first computer unit 12 serves at least for the control of medical devices, witch carry out safety-related and safety critical functions, respectively. In the FIGURE, these safety-related devices are indicated with reference numeral 20. For example, in the FIGURE, a pump 25, an insufflator 24 and RF generator 26 are shown. These exemplary enumeration of three devices is not to be understood in any limiting sense what is indicated in the FIGURE by further devices n and m. Furthermore, the first computer unit 12 may also be used for the control of non safety-related devices provided that respective tested software is used. However, this possibility will not be further discussed below.

The communication between the first computer unit 12 and the safety-related devices 20 is achieved via a bus-system 28 which allows a safe transmission of data. In view of this bus-system 28 other requirements with respect to fail safety has to be considered as is the case in the afore-mentioned Ethernet-bus 16. The applicant offers such a bus-system for example under the name Karl Storz-Communication-Bus (SCB®).

The system 10 further comprises a switching unit 30. The switching unit 30 is connected with its input side to the computer unit 12 and the computer unit 14, wherein in the FIGURE only one connection line 33, 35 each is exemplarily shown. It is to be understood that these connection lines 33, 35 comprise a plurality of single connection lines.

On the output side the switching unit 30 is connected with peripheral devices 40, wherein in the FIGURE a touch sensitive monitor 42 (called touch-screen), an input keyboard 44 as well as a mouse 46 are shown as an example. The peripheral devices 40 are located for example in the direct sphere of the surgeon in the operation room so that these peripheral devices 40 have to be adapted accordingly. The touch-screen 42 is for example provided with a sterile cover.

The connection of the peripheral devices 40 with the switching unit 30 is made via respective lines 48, wherein for simplification reasons only one line is shown each representing a plurality of connecting lines.

A switching unit 30 has the task to connect each peripheral device 42 to 46 with one of both computer units 12, 14 so that the input and the display, respectively, of data is possible.

The control of the switching unit 30 is provided by the first computer unit 12, and respective control signals may be transmitted to the switching unit 30 via a control line 38.

The second computer unit 14 is connected (indirect-coupled) with the devices 52 via an optical bus 50, which devices carry out non safety-related functions. Such functions are for example telephone remote control, room lighting, etc. The control of these non safety-related devices is hence achieved by the second computer unit 14.

As already mentioned, the first computer unit 12 is equipped with an embedded operating system. This should guarantee that interventions into the systems or manipulations of the systems from outside are not possible. The first computer unit 12 is rather a embodied as a closed system on which only tasks are running which are required for the control of the safety-related devices 20. Also, tasks may run additionally which serve to control the non safety-related devices 42 in case that these tasks are tested in view of safety aspects before.

The second computer unit 14 is however provided as a common medical PC. In contrast to the first computer unit 12 no tasks are allowed to run on the second computer unit 14, which tasks serve to control safety-related devices.

Both computer units 12, 14 supply data by the respective lines 33, 35 to the switching unit 30 and depending on the "position" of the switching unit only the data of one of both computer units are displayed on the touch-screen 42. Also the input of data is carried out only in this computer unit. In case that the surgeon wants to select for example functions of the other group of devices, he may do this via a respective input of an instruction which is either directly received by the first computer unit 12 or indirectly received via the computer unit 14 and the bus 16 by the first computer unit 12. In response thereto it transmits a respective control signal via the control line 38 causing a switching in the switching unit 30. On the touch-screen 42 the respective data, selecting menus etc. of the selected group of devices will than be displayed.

In case of a connection between the second computer unit 14 with the peripheral devices 40 it is necessary that any error messages relating to safety-related devices 20 are immediately signalized to the surgeon independent of the switch condition of the switching unit 30 via the touch-screen 42. For this, a task is running in the second computer unit 14 which continuously checks the messages sent by the first computer unit 12 via the bus 16 for failure messages. If an error message is detected the second computer unit 14 ensures that a window is opened on the touch-screen in which the error message is displayed.

A further task of the first computer unit 12 is to check the presence of the switching unit 30. If the switching unit 30 cannot be detected anymore by the first computer unit 12 for example due to breakdown, the first computer unit 12 must immediately generate an error message. This error message is to signalize the surgeon that an appropriate display and an input of data via the peripheral devices 40 may not be guaranteed anymore.

Further it is necessary that the first computer unit 12 checks the second computer unit 14 and in case of a failure the switching unit 30 is immediately set in those switching conditions in which the first computer unit 12 is connected with the peripheral devices 40.

Under safety aspects it is also necessary that when inputting an instruction for switching the peripheral devices 40 to the second computer unit 14 all not yet completed functions of the safety-related devices 20 are first completed with a respective display of the parameters. This is to guarantee that the execution of these safety-related functions is not terminated to early. In the reverse case, however the peripheral devices 40 are immediately connected with the first computer unit 12 so that a safety-related function may be carried out without any delay.

It is to be understood that the invention may be realized not only in form of the afore-mentioned embodiment but also in other embodiments. The scope of such modifications is only defined by the appended claims.

What is claimed is:

1. A method for the central control of devices used during an operation, the method comprising:
   using at least one safety-related device to perform safety-related functions;
   using at least one non-safety-related device to perform only non-safety-related functions;
   connecting a first control unit to a second control unit;
   using the first control unit embodied as a closed system to control at least the safety-related devices;
   using the second control unit embodied as an open system to control only non-safety-related; and
   controlling an interface unit with the first control unit to forward signals from the first or the second control unit to a common peripheral device;
   wherein the first control unit drives the interface unit upon an error of the second control unit such that the signals of the first control unit are forwarded to the peripheral device.

2. The method of claim 1, further comprising checking the second control unit for faults with the first control unit.

3. The method of claim 1, wherein the interface unit immediately forwards the signals of the first control unit to the peripheral device if a safety-related function is to be carried out.

4. The method of claim 3, wherein after activating a non-safety-related function the interface unit forwards the signals of the second control unit to the peripheral device only if the safety-related function is completed.

5. The method of claim 1, wherein the at least one non-safety-related device is located in an operating room.

6. The method of claim 5, wherein the second control unit is located in the operating room.

7. A method for the central control of devices used during an operation, the method comprising:
   providing at least one device that performs safety-related functions;
   providing at least one device that performs only non-safety-related functions;
   connecting a first control unit to the devices that perform safety-related functions;
   connecting a second control unit to the devices that perform only non-safety-related functions;
   connecting the first control unit to the second control unit;
   using the first control unit to control the safety-related functions performed by the devices connected to the first control unit;
   using the second control unit to control only the non-safety-related functions performed by the devices connected to the second control unit; and
   controlling an interface unit with the first control unit to forward signals from the first or the second control unit to a common peripheral device;
   wherein the first control unit drives the interface unit upon an error of the second control unit such that the signals of the first control unit are forwarded to the peripheral device.

8. A system for the central control of devices used during an operation, comprising:
   a plurality of devices including at least one device that performs safety-related functions and at least one device that performs only non-safety-related functions;
   a first control unit connected to the devices that perform safety-related functions, wherein said first control unit is embodied as a closed system that controls the devices that perform safety-related functions;
   a second control unit connected to the devices that perform only non-safety-related functions, wherein said second control unit is embodied as an open system that does not control any of the devices that perform safety-related functions, and wherein said second control unit is connected to said first control unit and exchanges information with said first control unit; and
   an interface unit and a common peripheral device, wherein said first control unit controls said interface unit to forward signals from said first or second control unit to the common peripheral device;
   wherein said first control unit drives said interface unit upon an error of said second control unit such that the signals of said first control unit are forwarded to said peripheral device.

9. The system of claim 8, wherein said first control unit checks said second control unit for faults.

10. The system of claim 8, wherein said interface unit immediately forwards the signals of said first control unit to said peripheral device if a safety-related function is to be carried out.

11. The system of claim 10, wherein after activating a non safety-related function said interface unit forwards the signals of said second control unit to said peripheral device only if the safety-related function is completed.

12. System of claim 8, further comprising a bus system by which said first control unit and said safety-related devices are interconnected.

13. System of claim 12, further comprising a second bus system by which said second control unit and said non safety-related devices are interconnected.

14. The system of claim 12, wherein said first control unit checks said second control unit for faults.

15. System of claim 8, further comprising an interface unit connected to said first and second control units.

16. System of claim 8, further comprising a touch-screen.

17. System of claim 8, wherein said second control unit comprises a receiving means to capture error messages from said first control unit.

18. The system of claim 8, wherein said safety-related devices-include at least one endoscopic device.

19. The system of claim 18, wherein said at least one endoscopic device includes at least one of an insufflator, a pump, a light source, or a video device.

20. The system of claim 8, wherein said non safety-related devices include at least one of a picture archiving device, OP-lighting, room lighting, a telephone, air conditioning, a pager, an internet connection, a hospital system, consumption parts, and a management system.

21. The system of claim 8, further comprising an Ethernet bus by which said first and second control units are interconnected.

22. The system of claim 8, wherein said first control unit comprises a voice control unit.

23. The system of claim 8, wherein said first and second control units comprise a dual processor computer unit.

24. The system of claim 8, wherein the at least one device that performs only non-safety-related functions is located in an operating room.

25. The system of claim 24, wherein the second control unit is located in the operating room.

26. A system for the central control of both safety-related devices and non-safety-related devices during an operation, comprising:
   a first control unit that is configured to operate as a closed system to control the safety-related devices when the safety related devices are connected thereto;

a second control unit that is configured to operate as an open system to control the non-safety-related devices when the non-safety-related devices are connected thereto;

wherein said second control unit is configured to control only the non-safety-related devices; and wherein said second control unit is connected to said first control unit and exchanges information with said first control unit; and an interface unit and a common peripheral device, wherein said first control unit controls said interface unit to forward signals from said first or second control unit to the common peripheral device;

wherein said first control unit drives said interface unit upon an error of said second control unit such that the signals of said first control unit are forwarded to said peripheral device.

* * * * *

UNITED STATES PATENT AND TRADEMARK OFFICE
CERTIFICATE OF CORRECTION

PATENT NO.          : 7,485,114 B2
APPLICATION NO.     : 10/379152
DATED               : February 3, 2009
INVENTOR(S)         : Heinz-Werner Stiller et al.

Page 1 of 1

It is certified that error appears in the above-identified patent and that said Letters Patent is hereby corrected as shown below:

Title page, item (75) Inventor: should read as follows Heinz-Werner Stiller, Jestetten, (DE).

Signed and Sealed this

Twenty-eighth Day of April, 2009

JOHN DOLL
*Acting Director of the United States Patent and Trademark Office*